United States Patent
Schmitt

(10) Patent No.: US 11,530,187 B2
(45) Date of Patent: Dec. 20, 2022

(54) METHOD FOR PRODUCING (5S)-4-[5-(3,5-DICHLOROPHENYL)-5-(TRIFLUORO-METHYL)-4H-ISOXAZOL-3-YL]-2-METHYL-BENZOIC ACID

(71) Applicant: Intervet Inc., Madison, NJ (US)

(72) Inventor: Harald Schmitt, Mainz (DE)

(73) Assignee: Intervet Inc., Madison, NJ (US)

( * ) Notice: Subject to any disclaimer, the term of this patent is extended or adjusted under 35 U.S.C. 154(b) by 2 days.

(21) Appl. No.: 17/414,228

(22) PCT Filed: Dec. 20, 2019

(86) PCT No.: PCT/EP2019/086538
§ 371 (c)(1),
(2) Date: Jun. 15, 2021

(87) PCT Pub. No.: WO2020/127878
PCT Pub. Date: Jun. 25, 2020

(65) Prior Publication Data
US 2022/0048874 A1    Feb. 17, 2022

(30) Foreign Application Priority Data
Dec. 21, 2018  (EP) ..................... 18215376

(51) Int. Cl.
*C07D 261/04*    (2006.01)

(52) U.S. Cl.
CPC ................... *C07D 261/04* (2013.01)

(58) Field of Classification Search
CPC ..................................................... C07D 261/04
See application file for complete search history.

(56) References Cited

FOREIGN PATENT DOCUMENTS

| EA | 022114 B1 | 11/2015 |
| JP | 2011051977 A | 3/2011 |
| JP | 5679102 B2 | 3/2015 |
| WO | 2011067272 A1 | 6/2011 |
| WO | 2014090918 A1 | 6/2014 |

OTHER PUBLICATIONS

English translation of JP2011051977 Abstract.
Complete human translation for JP5679102B2., 14 pages.
European Search Report for EP18215376.7 dated Apr. 4, 2019, 6 pages.
Machine translation for JP5679102B2, retrieved from Google Patents on Apr. 10, 2019.

*Primary Examiner* — Shawquia Jackson
(74) *Attorney, Agent, or Firm* — David J. Kerwick

(57) ABSTRACT

The present invention relates to a novel method for preparing (5S)-4-[5-(3,5-dichlorophenyl)-5-(trifluoromethyl)-4H-isoxazol-3-yl]-2-methyl-benzoic acid, which can preferably be used in the synthesis of (5S)-4-[5-(3,5-dichlorophenyl)-5-(trifluoromethyl)-4H-isoxazol-3-yl]-N-[2-oxo-2-(2,2,2-trifluoroethylamino)ethyl]-2-methyl-benzamide.

16 Claims, No Drawings

METHOD FOR PRODUCING (5S)-4-[5-(3,5-DICHLOROPHENYL)-5-(TRIFLUORO-METHYL)-4H-ISOXAZOL-3-YL]-2-METHYL-BENZOIC ACID

CROSS-REFERENCE TO RELATED APPLICATIONS

This application is a national stage entry under 35 U.S.C. § 371 of PCT/EP2019/086538 filed on Dec. 20, 2019, which claims priority to EP18215376.7 filed on Dec. 21, 2018, the content of PCT/EP2019/086538 is hereby incorporated by reference in its entirety.

The present invention relates to a novel method for preparing (5S)-4-[5-(3,5-dichloro-phenyl)-5-(trifluoromethyl)-4H-isoxazol-3-yl]-2-methyl- benzoic acid, which can preferably be used in the synthesis of (5S)-4-[5-(3,5-dichlorophenyl)-5-(trifluoromethyl)-4H-isoxazol-3-yl]-N-[2-oxo-2-(2,2,2-trifluoroethylamino)ethyl]-2- methyl-benzamide.

BACKGROUND OF THE INVENTION (5RS)-4-[5-(3,5-dichlorophenyl)-5-(trifluoromethyl)-4H-isoxazol-3-yl]-N-[2-oxo-2-(2,2,2-trifluoroethylamino) ethyl]-2- methyl-benzamide (hereinafter referred to as fluralaner) is a synthetic insecticide which is represented by the following Formula (A).

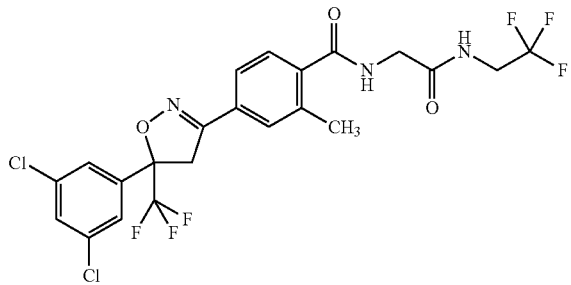

Formula (A)

Fluralaner is a systemic active ingredient agent that can be administered orally. The active ingredient is reported to antagonistically inhibit chloride channels via bonding to gamma aminobutyric acid (GABA) and/or glutamate receptors in the nervous system of several arthropods. Since fluralaner does not show an analogous bonding in the nervous systems of mammals, it is for example suitable for flea, mite and tick treatment in mammals, for example in dogs and cats.

Fluralaner is a racemate. The (S)-enantiomer is reported to be the eutomer substantially contributing to the antiparasitic activity of the active ingredient. In view thereof, the use of enantio-pure or enantio-enriched (S)-fluralaner is considered to be advantageous in comparison to racemic fluralaner.

(5RS)-4-[5-(3,5-dichlorophenyl)-5-(trifluoromethyl)-4H-isoxazol-3-yl]-2-methyl-benzoic acid acid (IOBA) is a key intermediate in the synthesis of fluralaner and said compound is represented by the following Formula (1)

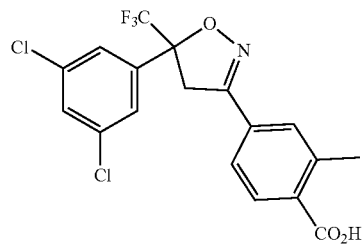

Formula (1)

Since enantio-pure or enantio-enriched (S)-fluralaner might be considered as advantageous as active ingredient, the isolation of an enantio-pure or enantio-enriched (5S)-4-[5-(3,5-dichlorophenyl)-5-(trifluoromethyl)-4H-isoxazol-3-yl]-2-methyl-benzoic acid (S-IOBA) would be desirable. (5S)-4-[5-(3,5-dichlorophenyl)-5-(trifluoromethyl)-4H-isoxazol-3-yl]-2-methyl-benzoic acid is represented by the following Formula (1a)

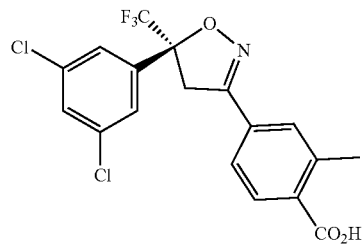

Formula (1a)

WO 2014/090918 A1 describes that the separation of a similar compound into the enantiomer can be performed by chiral column chromatography or by diastereomeric recrystallisation. More particularly, said document describes that a similar compound, racemic 3-methyl-5-[(5RS)-5-(3,4,5-trichlorophenyl)-5-(trifluoromethyl)-4H-isoxazol-3-yl]thiophene-2-carboxylic acid (IOTA), is treated with (R)-1-(4-methylphenyl)ethylamine in a ternary mixture of water, acetonitrile and 2-butanol to obtain a precipitate of the corresponding (S)-isoxazoline thiophene carbolic acid salt with, after washing, a chiral purity of over 95%, which can be enhanced to over 98% by a further recrystallisation step. This process however uses a ternary mixture of solvents for the crystallisation.

Furthermore, in WO 2014/090918 A1, in case one wants to racemize the "by-product" (R)-isoxazoline thiophene carboxylic acid which has remained in said ternary mixture, one needs to change this ternary solvent mixture to another solvent. In addition, it was found that treating racemic IOBA with (R)-1-(4-methylphenyl)ethylamine did not result in any precipitation of either (R)-IOBA or (S)-IOBA.

JP 05679102 describes that a process according to which a racemic isoxazoline benzoic acid derivative can be separated into its enantiomers, wherein the process is carried out in an organic solvent or a mixture thereof and an active basic compound is used. In particular, racemic (5RS)-4-[5-(3,5-dichlorophenyl)-5-(trifluoromethyl)-4H-isoxazol-3-yl]-2-methyl-benzoic acid and an optically active α-phenylethylamine were reacted in a mixture of toluene and ethyl acetate or just ethyl acetate to obtain a precipitate being the corresponding enantiomeric salt of (5S)-4-[5-(3,5-dichlorophenyl)-5-(trifluoromethyl)-4H-isoxazol-3-yl]-2-methyl-benzoic acid and (S)-α-phenylethylamine in a ratio of 1:1.

However there still exists a need for a new route of synthesis, i.e. for a method of preparing (5S)-4-[5-(3,5-dichlorophenyl)-5-(trifluoromethyl)-4H-isoxazol-3-yl]-2-methyl-benzoic acid, which can preferably be applied in a simple and effective manner.

Hence, it is an object of the present invention to overcome one or more of the drawbacks of the above-mentioned processes. In particular, it is an object of the present invention to provide a method for preparing (5S)-4-[5-(3,5-dichlorophenyl)-5-(trifluoromethyl)-4H-isoxazol-3-yl]-2-methyl-benzoic acid with a high enantiomeric excess. Another object is to provide a method for preparing (5S)-4-[5-(3,5-dichlorophenyl)-5-(trifluoromethyl)-4H-isoxazol-3-yl]-2-methyl-benzoic acid with an advantageous high yield, in particular when used in a large-scale process. It is further an object of the present invention to provide a method for preparing (5S)-4-[5-(3,5-dichlorophenyl)-5-(trifluoromethyl)-4H-isoxazol-3-yl]-2-methyl-benzoic acid with a simple solvent system. It is furthermore an object of the present invention to provide a method for preparing (5S)-4-[5-(3,5-dichlorophenyl)-5-(trifluoromethyl)-4H-isoxazol-3-yl]-2-methyl-benzoic acid wherein the same solvent system as for the precipitation of (S)-IOBA can be used for the racemisation of (R)-IOBA.

The present invention has unexpectedly solved at least one of the above objectives by the provision of a new synthetic approach for preparing a compound according to Formula (1a).

Hence, the subject of the present invention is a method for preparing (5S)-4-[5-(3,5-dichlorophenyl)-5-(trifluoromethyl)-4H-isoxazol-3-yl]-2-methyl-benzoic acid according to Formula (1a)

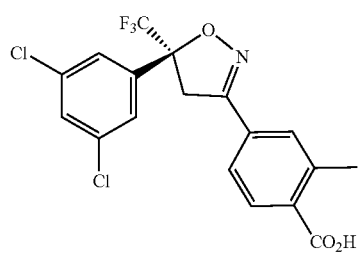

Formula (1a)

from (5RS)-4-[5-(3,5-dichlorophenyl)-5-(trifluoromethyl)-4H-isoxazol-3-yl]-2-methyl-benzoic acid according to Formula (1)

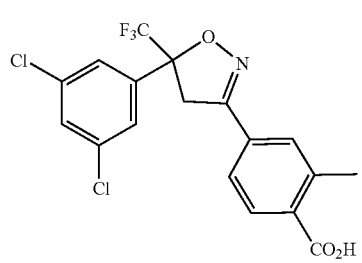

Formula (1)

comprising the steps of:
(i) reacting (5RS)-4-[5-(3,5-dichlorophenyl)-5-(trifluoromethyl)-4H-isoxazol-3-yl]-2-methyl-benzoic acid with a compound of Formula (2A), (2B) or (2C)

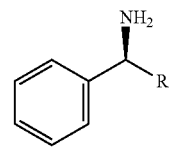

Formula (2A)

wherein R is an alkyl with 1 or 2 carbon atoms,

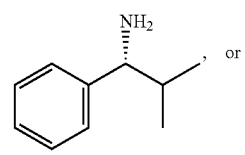

Formula (2B)

, or

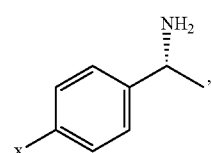

Formula (2C)

wherein X is Cl or Br,
in an organic solvent having a polarity $E_T(30)$ between 130 and 175 kJ/mol to form a precipitate and a supernatant solution
(ii) separating the precipitate from step (i) from the supernatant solution
(iii) treating the precipitate from step (ii) with acidic aqueous solution, and
(iv) separating (S)-4-[5-(3,5-dichlorophenyl)-5-(trifluoromethyl)-4H-isoxazol-3-yl]-2-methyl-benzoic acid from the acidic aqueous solution of step (iii),
under the proviso that, when R is methyl, the solvent in step (i) is not ethyl acetate.

It was unexpectedly found that the method of the present invention allows advantageous yields of the resulting compound with a high enantiomeric excess. Additionally, the method can be carried out without sophisticated equipment and the need of a chromatographic purification step is avoided.

DETAILED DESCRIPTION OF THE INVENTION

The present invention relates to a method for preparing a compound according to Formula (1a) comprising steps (i), (ii), (iii) and (iv). In a preferred embodiment of the invention and/or embodiments thereof of the invention the above-mentioned steps (i), (ii), (iii) and (iv)) can be carried out consecutively.

The compound according to Formula (1a) is the (S)-enantiomer of the compound according to Formula (1), (5RS)-4-[5-(3,5-dichlorophenyl)-5-(trifluoromethyl)-4H-isoxazol-3-yl]-2-methyl-benzoic acid, wherein the compound according to Formula (1) can for example be prepared as described in synthetic example 3 of US 2007/0066617.

In step (i) of the method according to the invention and/or any embodiment thereof (5RS)-4-[5-(3,5-dichlorophenyl)-5-(trifluoromethyl)-4H-isoxazol-3-yl]-2-methyl-benzoic acid is reacted with a compound of Formula (2A), (2B) or (2C) in an organic solvent having a polarity $E_T(30)$ between 130 and 175 kJ/mol to form a precipitate and a supernatant solution.

In Formula (2A) residue R is an alkyl with one or two carbon atoms.

In a preferred embodiment of the invention and/or embodiments thereof residue R is an alkyl with one carbon atom, i.e. residue R is methyl. The corresponding base or alkaline compound is (S)-1-phenylethylamine.

In an alternatively preferred embodiment of the invention and/or embodiments thereof residue R is an alkyl with two carbon atoms, i.e. residue R is ethyl. The corresponding base or alkaline compound is (S)-1-phenylpropylamine.

The compound according to Formula (2B) is (R)-1-phenyl-2-methyl-propylamine.

In Formula (2C) residue X is Cl or Br.

In a preferred embodiment of the invention and/or embodiments thereof residue X in Formula (2C) is Cl and the corresponding base or alkaline compound is (R)-1-(4-chlorophenyl)-ethylamine.

In a more preferred embodiment residue X in Formula (2C) is Br and the corresponding base or alkaline compound is (R)-1-(4-bromophenyl)-ethylamine.

In a preferred embodiment of the invention and/or embodiments thereof the compound of Formula (2A), (2B) or (2C) is selected from the group consisting of (S)-1-phenylpropylamine, (R)-1-phenyl-2-methyl-propylamine, (R)-1-(4-chlorophenyl)-ethylamine and (R)-1-(4-bromophenyl)-ethylamine.

In a preferred embodiment of the invention and/or embodiments thereof (5RS)-4-[5-(3,5-dichlorophenyl)-5-(trifluoromethyl)-4H-isoxazol-3-yl]-2-methyl-benzoic acid is reacted in step (i) with a compound of Formula (2A), (2B) or (2C) in a molar ratio of between 1:0.4 and 1:5, preferably between 1:0.5 and 1:3, more preferably between 1:0.6 and 1:2, in particular between 1:0.7 and 1:1.

An organic solvent is a liquid compound that dissolves, preferably completely dissolves, a substance to form a solution. Examples of organic solvents are well known in the art.

Organic solvents can be classified in categories, for example with their boiling points (high or low boing solvents), their acidity/basicity (acidic or alkaline solvents) and or their polarity (polar and non-polar solvents).

The $E_T(30)$ value is regarded to indicate the polarity of different solvents (see for example Jose P. Ceron-Carrasco et al.: "Solvent polarity scales: determination of new $E_T(30)$ values for 84 organic solvents", Research Article; Journal of Physical Organic Chemistry, 2014, 27, pages 512-518). The $E_T(30)$ value is determined with the help of the negative solvatochromic dye 2,6-diphenyl-4-(2,4,6-triphenylpyridin-1-ium-1-yl)phenolate, which is also referred to as Betaine 30 or Reichhardt's dye. Betaine 30 is represented by the compound according to below Formula (B)

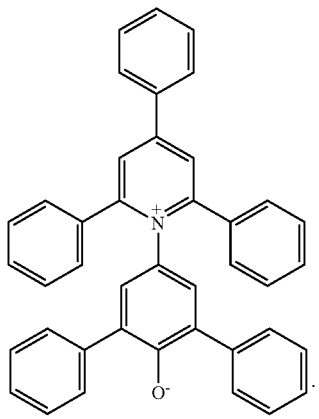

Formula (B)

More specifically, the $E_T(30)$ value is determined with the help of Betaine 30 in the corresponding solvent through the longest wavelength VIS/NIR adsorption band. High $E_T(30)$ values are considered to correspond to a high polarity of the solvent, whereas low $E_T(30)$ values indicate low polarity of the solvent. Thus, in short, the higher the $E_T(30)$ value, the more polar the solvent and vice versa. The $E_T(30)$ value is also defined as the molar electronic excitation energy and calculated as follows $$E_T(30) = \frac{119627 \text{kJ} \cdot \text{nm} \cdot \text{mol}^{-1}}{\lambda_{max}}$$

wherein $\lambda_{max}$ is the long-wavelength adsorption band in the visible/near IR-region of Betaine 30 in the corresponding solvent, when measured at 25° C. and 101 kPa.

In step (i) of the present method the organic solvent has an $E_T(30)$ value between 130 and 175 kJ/mol.

Examples of solvents having an $E_T(30)$ value between 130 and 175 kJ/mol are aliphatic, cycloaliphatic or aromatic ethers such as ethylene glycol dimethyl ether, triethylene glycol dimethyl ether, 1,2-dimethoxyethane, di-n-butyl ether, di-tert.butyl ether, di-isopropyl ether, n-butyl methyl ether, methyl tert-butyl ether, cyclopentyl methyl ether, dioxane, tetrahydropyran, 2,2,5,5-tetramethyltetrahydropyran, tetrahydrofuran, tetra-hydro-2-methylfuran, 2,2,5,5-tetramethyltetrahydrofuran, benzyl methyl ether, dibenzyl ether, anisole, 3-methyl anisole and phenetole; arenes and pyridines such as benzene, toluene, m-xylene and mesitylene; haloarenes such as chlorobenzene, 1,3-dichlorobenzene, bromobenzene and 1,3 dibromobenzene and pyridine; aliphatic esters such as methyl formate, methyl acetate, methyl propanoate, methyl butanoate, methyl hexanoate, ethyl formate, ethyl acetate, ethyl propanoate, ethyl benzoate and butyl acetate; aliphatic, cycloalipatic or aromatic amines such as diethylamine, triethylamine, diisopropylamine, morpholine, piperidine; haloalkanes such as trichloromethane, tetrachloromethane, 1,1-dichloroethane, 1,2-dichloroethane and 1,1,2,2-tetrachlorethane and mixtures thereof.

In a preferred embodiment of the invention and/or embodiments thereof the organic solvent has an $E_T(30)$ value between 132 and 175 kJ/mol. Preferably between 134 and 174 kJ/mol, more preferably 135 and 170 kJ/mol, in particular between 140 and 165, and more in particular between 134 and 160 kJ/mol.

In a preferred embodiment of the invention and/or embodiments thereof the organic solvent is an aliphatic or cycloaliphatic ether such as ethylene glycol dimethyl ether, triethylene glycol dimethyl ether, 1,2-dimethoxyethane, di-n-butyl ether, di-tert-butyl ether, di-isopropyl ether, n-butyl methyl ether, methyl tert-butyl ether, cyclopentyl methyl ether, dioxane, tetrahydrofuran, tetrahydro-2-methylfuran; an arene such as benzene, toluene, m-xylene, mesitylene, a haloarene such as chlorobenzene, bromobenzene; an aliphatic ester such as methyl acetate, methyl propanoate, methyl butanoate, ethyl acetate, ethyl propanoate, ethyl benzoate, butyl acetate; an aliphatic amine such as diethylamine, triethylamine, diisopropylamine; a haloalkane such as trichloromethane, tetrachloromethane, 1,1 dichloroethane and 1,2-dichloroethane and mixtures thereof.

In a preferred embodiment of the invention and/or embodiments thereof the organic solvent selected from the group consisting of methyl tert-butyl ether, cyclopentyl methyl ether, tetrahydrofuran, dioxane, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof the organic solvent is methyl tert-butyl ether. In a preferred embodiment of the invention and/or embodiments thereof the organic solvent is cyclopentyl methyl ether. In a preferred embodiment of the invention and/or embodiments thereof the organic solvent is tetrahydrofuran. In a preferred embodiment of the invention and/or embodiments thereof the organic solvent is dioxane. In a preferred embodiment of the invention and/or embodiments thereof the organic solvent is chlorobenzene. In a preferred embodiment of the invention and/or embodiments thereof the organic solvent is toluene. In a preferred embodiment of the invention and/or embodiments thereof the organic solvent is m-xylene. In a preferred embodiment of the invention and/or embodiments thereof the organic solvent is mesitylene. In a preferred embodiment of the invention and/or embodiments thereof the organic solvent is ethyl acetate. In a preferred embodiment of the invention and/or embodiments thereof the organic solvent is butyl acetate. In a preferred embodiment of the invention and/or embodiments thereof the organic solvent is triethylamine. In a preferred embodiment of the invention and/or embodiments thereof the organic solvent is trichloromethane. In a preferred embodiment of the invention and/or embodiments thereof the organic solvent is 1,2-dichloroethane.

In a preferred embodiment of the invention and/or embodiments thereof the organic solvent selected from the group consisting of methyl tert-butyl ether, cyclopenty methyl ether, tetrahydrofuran, dioxane, chlorobenzene, toluene, m-xylene, mesitylene, butyl acetate, triethylamine, trichloromethane, 1,2-dichloroethane and mixtures thereof.

In a preferred embodiment of the invention and/or embodiments thereof residue R of Formula (2A) in step (i) is methyl and the organic solvent is selected from the group consisting of methyl tertbutyl ether, cyclopentyl methyl ether, tetrahydrofuran, dioxane, chlorobenzene, toluene, m-xylene, mesitylene, butyl acetate, triethylamine, trichloromethane, 1,2-dichloroethane and mixtures thereof.

In a preferred embodiment of the invention and/or embodiments thereof residue R of Formula (2A) in step (i) is methyl and the organic solvent is selected from the group consisting of methyl tertbutyl ether, cyclopentyl methyl ether, dioxane, chlorobenzene, toluene, m-xylene, mesitylene, butyl acetate, triethylamine, trichloromethane, 1,2-dichloroethane and mixtures thereof.

In a preferred embodiment of the invention and/or embodiments thereof residue R of Formula (2A) in step (i) is methyl and the organic solvent is selected from the group consisting of dioxane, chlorobenzene, toluene, butyl acetate, triethylamine, trichloromethane, 1,2-dichloroethane and mixtures thereof.

In a preferred embodiment of the invention and/or embodiments thereof residue R of Formula (2A) in step (i) is methyl and the organic solvent is methyl tert-butyl ether, or residue R of Formula (2A) in step (i) is methyl and the organic solvent is cyclopentyl methyl ether, or residue R of Formula (2A) in step (i) is methyl and the organic solvent is tetrahydrofuran, or residue R of Formula (2A) is methyl and the organic solvent is dioxane, or residue R of Formula (2A) is methyl and the organic solvent is chlorobenzene, or residue R of Formula (2A) is methyl and the organic solvent is toluene, or residue R of Formula (2A) is methyl and the organic solvent is m-xylene, or residue R of Formula (2A) is methyl and the organic solvent is mesitylene, or residue R of Formula (2A) is methyl and the organic solvent is butyl acetate, or residue R of Formula (2A) is methyl and the organic solvent is triethylamine, or residue R of Formula (2A) is methyl and the organic solvent is trichloromethane or residue R of Formula (2A) is methyl and the organic solvent is 1,2-dichloroethane.

In a preferred embodiment of the invention and/or embodiments thereof residue R of Formula (2A) in step (i) is ethyl and the organic solvent is selected the group consisting of methyl tert-butyl ether, cyclopentyl methyl ether, tetrahydrofuran, dioxane, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof residue R of Formula (2A) in step (i) is ethyl and the organic solvent is selected the group consisting of methyl tert-butyl ether, cyclopentyl methyl ether, dioxane, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof residue R of Formula (2A) in step (i) is ethyl and the organic solvent is selected the group consisting of methyl tert-butyl ether, cyclopentyl methyl ether, dioxane, chlorobenzene, toluene, m-xylene, mesitylene, ethyl acetate, butyl acetate, triethylamine, 1,2-dichloroethane and mixtures thereof.

In a preferred embodiment of the invention and/or embodiments thereof residue R of Formula (2A) in step (i) is ethyl and the organic solvent is selected the group consisting of methyl tert-butyl ether, cyclopentyl methyl ether, chlorobenzene, m-xylene, mesitylene, ethyl acetate, butyl acetate, triethylamine, 1,2-dichloroethane and mixtures thereof.

In a preferred embodiment of the invention and/or embodiments thereof, residue R of Formula (2A) in step (i) is ethyl and the organic solvent is methyl tert-butyl ether, or residue R of Formula (2A) in step (i) is ethyl and the organic solvent is cyclopentyl methyl ether, or residue R of Formula (2A) in step (i) is ethyl and the organic solvent is tetrahydrofuran, or residue R of Formula (2A) is ethyl and the organic solvent is dioxane, or residue R of Formula (2A) is ethyl and the organic solvent is chlorobenzene, or residue R of Formula (2A) is ethyl and the organic solvent is toluene, or residue R of Formula (2A) is ethyl and the organic solvent is m-xylene, or residue R of Formula (2A) is ethyl and the organic solvent is mesitylene, or residue R of Formula (2A) is ethyl and the organic solvent is ethyl acetate, or residue R of Formula (2A) is ethyl and the organic solvent is butyl acetate, or residue R of Formula (2A) is ethyl and the organic solvent is triethylamine, or residue R of Formula (2A) is ethyl and the organic solvent is trichloromethane or residue R of Formula (2A) is ethyl and the organic solvent is 1,2-dichloroethane.

In a preferred embodiment of the invention and/or embodiments thereof the chiral base in step (i) is (R)-1-phenyl-2-methyl-propylamine (Formula 2B) and the organic solvent is tetrahydrofuran, or the chiral base is (R)-1-phenyl-2-methyl-propylamine (Formula 2B) and the organic solvent is dioxane, or the chiral base is (R)-1-phenyl-2-methyl-propylamine (Formula 2B) and the organic solvent is toluene, or the chiral base is (R)-1-phenyl-2-methyl-propylamine (Formula 2B) and the organic solvent is ethyl acetate, or the chiral base is (R)-1-phenyl-2-methyl-propylamine (Formula 2B) and the organic solvent is 1,2-dichloroethane.

In a preferred embodiment of the invention and/or embodiments thereof the chiral base in step (i) is (R)-1-phenyl-2-methyl-propylamine (Formula 2B) and the organic solvent is selected from the group consisting of methyl tert-butyl ether, cyclopentyl methyl ether, tetrahydrofuran, dioxane, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof the chiral base in step (i) is (R)-1-phenyl-2-methyl-propylamine (Formula 2B) and the organic solvent is selected from the group consisting of methyl tert-butyl ether, cyclopentyl methyl ether, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof the chiral base in step (i) is (R)-1-phenyl-2-methyl-propylamine (Formula 2B) and the organic solvent is selected from the group consisting of chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof the chiral base in step (i) is (R)-1-phenyl-2-methyl-propylamine (Formula 2B) and the organic solvent is selected from the group consisting of chlorobenzene, toluene, ethyl acetate, butyl acetate, triethylamine, trichloromethane, 1,2-dichloroethane and mixtures thereof.

In a preferred embodiment of the invention and/or embodiments thereof residue X of Formula (2C) in step (i) is Cl (chloride) or Br (bromide).

In a preferred embodiment of the invention and/or embodiments thereof residue X of Formula (2C) in step (i) is Cl and the organic solvent is selected from the group consisting of tetrahydrofuran, dioxane, toluene, ethyl acetate and mixtures thereof.

In a preferred embodiment of the invention and/or embodiments thereof residue X of Formula (2C) in step (i) is Cl and the organic solvent is selected from the group consisting of methyl tert-butyl ether, cyclopentyl methyl ether, dioxane, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof residue X of Formula (2C) in step (i) is Cl and the organic solvent is selected from the group consisting of methyl tert-butyl ether, cyclopentyl methyl ether, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof residue X of Formula (2C) in step (i) is Cl and the organic solvent is selected from the group consisting of chlorobenzene, toluene, ethyl acetate, butyl acetate, triethylamine, trichloromethane, 1,2-dichloroethane and mixtures thereof.

In a preferred embodiment of the invention and/or embodiments thereof residue X of Formula (2C) in step (i) is Cl and the organic solvent is selected from the group consisting of toluene, ethyl acetate and mixtures thereof.

In a preferred embodiment of the invention and/or embodiments thereof residue R of Formula (2C) in step (i) is chloride and the organic solvent is tetrahydrofuran, residue R of Formula (2C) is chloride and the organic solvent is dioxane, residue R of Formula (2C) is chloride and the organic solvent is toluene, or residue R of Formula (2C) is chloride and the organic solvent is ethyl acetate.

In a preferred embodiment of the invention and/or embodiments thereof residue X of Formula (2C) in step (i) is Brand the organic solvent is selected from the group consisting of tetrahydrofuran, dioxane, toluene, ethyl acetate and mixtures thereof.

In a preferred embodiment of the invention and/or embodiments thereof residue R of Formula (2C) in step (i) is bromide and the organic solvent is tetrahydrofuran, residue R of Formula (2C) is bromide and the organic solvent is dioxane, residue R of Formula (2C) is bromide and the organic solvent is toluene, or residue R of Formula (2C) is bromide and the organic solvent is ethyl acetate.

In a preferred embodiment of the invention and/or embodiments thereof residue X of Formula (2C) in step (i) is Brand the organic solvent is selected from the group consisting of methyl tert-butyl ether, cyclopentyl methyl ether, dioxane, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof residue X of Formula (2C) in step (i) is Brand the organic solvent is selected from the group consisting of methyl tert-butyl ether, cyclopentyl methyl ether, chlorobenzene, toluene, m-xylene, mesitylene, ethyl acetate, butyl acetate, triethylamine, trichloromethane, 1,2-dichloroethane and mixtures thereof.

In a preferred embodiment of the invention and/or embodiments thereof residue X of Formula (2C) in step (i) is Brand the organic solvent is selected from the group consisting of chlorobenzene, toluene, ethyl acetate, butyl acetate, triethylamine, trichloromethane, 1,2-dichloroethane and mixtures thereof.

In a preferred embodiment of the invention and/or embodiments thereof residue X of Formula (2C) in step (i) is Brand the organic solvent is selected from the group consisting of toluene, ethyl acetate and mixtures thereof.

In step (i) (5RS)-4-[5-(3,5-dichlorophenyl)-5-(trifluoromethyl)-4H-isoxazol-3-yl]-2-methyl-benzoic acid is reacted with a compound of Formula (2A), (2B) or (2C) in an organic solvent having a polarity $E_T(30)$ between 130 and 175 kJ/mol to form a precipitate and a supernatant solution. Thus, in the organic solvent (5RS)-4-[5-(3,5-dichlorophenyl)-5-(trifluoromethyl)-4H-isoxazol-3-yl]-2-methyl-benzoic, preferably (S)-4-[5-(3,5-dichloro-phenyl)-5-(trifluoromethyl)-4H-isoxazol-3-yl]-2-methyl-benzoic acid, and a compound of Formula (2A), (2B) or (2C) are acting mutually on each other to form a product which precipitates and a supernatant solution. In other words, (5RS)-4-[5-(3,5-dichlorophenyl)-5-(trifluoromethyl)-4H-isoxazol-3-yl]-2-methyl-benzoic acid, preferably (5S)-4-[5-(3,5-dichlorophenyl)-5-(trifluoromethyl)-4H-isoxazol-3-yl]-2-methyl-benzoic acid, and a compound of Formula (2A), (2B) or (2C) react with each other to form a solid product which can precipitate, preferably completely precipitate, from the reaction mixture, while a supernatant solution remains. Said supernatant solution preferably contains a small part of the unreacted (5S)-4-[5-(3,5-dichlorophenyl)-5-(trifluoromethyl)-4H-isoxazol-3-yl]-2-methyl-benzoic acid, and preferably a large part of (5R)-4-[5-(3,5-dichlorophenyl)-5-(trifluoromethyl)-4H-isoxazol-3-yl]-2-methyl-benzoic acid.

Reacting (5RS)-4-[5-(3,5-dichlorophenyl)-5-(trifluoromethyl)-4H-isoxazol-3-yl]-2-methyl-benzoic acid with a compound of Formula (2A), (2B) or (2C) can be carried out at any temperature as long as the solvent is in a liquid state. For example, the reaction can be carried out at a temperature between 4 and 65° C., preferably between 10 and 55° C., also preferred between 15 and 45° C., preferably between 20 and 40° C., preferably between 25 and 35° C., and most preferred at about 23° C. (also referred to as room temperature).

In a preferred embodiment of the invention and/or embodiments thereof step (i) comprises heating (5RS)-4-[5-(3,5-dichlorophenyl)-5-(trifluoromethyl)-4H-isoxazol-3-yl]-2-methyl-benzoic acid with a compound of Formula (2A), (2B) or (2C) to an elevated temperature. An elevated temperature is a temperature from 23° C. (room temperature) to the boiling temperature of the organic solvent, preferably from 30° C. to the boiling temperature of the organic solvent minus 5° C., more preferably from 40° to the boiling temperature of the organic solvent minus 20° C. That means that in case toluene with a boiling temperature or boiling point of 111° C. is used as organic solvent, the reaction in step (i)) can be preferably carried out at from 23° C. to 111° C., preferably from 30° C. to 105° C., more preferably from 40° C. to 95° C. All temperatures as indicated herein and relating to boiling temperatures or boiling points relate to temperatures measured at normal pressure of 101 kPa.

Further, step (i) preferably comprises cooling the reacting mixture of said step. In case that step (i) does not comprise heating the reacting mixture to an elevated temperature, the reaction mixture can be cooled to 0° C. to 20° C., preferably about 10° C. In case that step (i) comprises heating the reaction mixture to an elevated temperature, the reaction mixture can be preferably cooled down to 0° C. to 40° C., preferably 10° C. to 30° C., in particular to about 23° C. (room temperature). By cooling the reaction mixture the obtained product forms a precipitate and a supernatant solution, wherein the supernatant solution preferably comprises (5R)-4-[5-(3,5-dichlorophenyl)-5-(trifluoromethyl)-4H-isoxazol-3-yl]-2-methyl-benzoic acid.

Further, the reaction of step (i) can be preferably subjected to a mechanical movement such as stirring or ultrasonic treatment.

In a preferred embodiment of the invention and/or embodiments thereof the duration of step (i) can be between 15 minutes and 24 hours, preferably between 30 minutes and 12 hours, in particular between 1 hour and 6 hours.

In step (ii) the precipitate from step (i) is separated from the supernatant solution. The precipitate from step (i) is a solid and can be separated from the supernatant solution by any method for separating a solid from a liquid. Examples of these methods are decanting or pouring off the supernatant solution, optionally with a preceding centrifugation step, and filtration.

In a preferred embodiment of the invention and/or embodiments thereof in step (ii) the separation of the precipitate from step (i) from the supernatant solution is carried out via filtration. A filtration as used herein is a mechanical or physical operation that separates a solid, in the present case the precipitate, from a liquid, in the present case the supernatant solution, via a medium through which only the fluid can pass. Such a medium might be referred to as a filter or sieve, preferably a filter. Examples of suitable filters are suction filters, press filters or folded filters, preferably suction filters.

In a preferred embodiment of the invention and/or embodiments thereof the precipitate from step (i), which has been separated from the supernatant solution, can be further subjected to a purification step. Such a purification step can preferably include washing the precipitate from step (i), for example with the organic solvent as used in step (i) of the present method. By doing this, optional residual adhering supernatant solution might be removed.

In step (ii), the precipitate from step (i), which has been separated from the supernatant solution, can preferably further be dried to remove residual solvents. Drying can preferably be conducted at a temperature of 23° C. to 50° C., preferably about 40° C. and/or at a reduced pressure of 1 kPa to 90 kPa; preferably about 10 kPa.

In step (iii) the precipitate from step (ii) is treated with an acidic aqueous solution. Herein the acidic aqueous solution is a solution having a pH value of less than 7.

Further, the acidic aqueous solution can preferably be obtained by the reaction of a Bronsted acid with water.

In a preferred embodiment of the invention and/or embodiments thereof the acidic aqueous solution in step (iii) is a solution of an acid having a pKa of 3.5 or less, preferably a pKa of 3.0 or less, more preferably a pKa of 2.5 or less, in particular a pKa of 2.0 or less.

Examples of suitable acids having a pKa of 3.5 or less are hydrogen chloride (the corresponding acid is hydrochloric acid), hydrogen bromide, hydrogen iodide, nitric acid, sulfuric acid, sodium or potassium hydrogen sulfate, phosphoric acid, trichloro acetic acid, fumaric acid, maleic acid, oxalic acid, citric acid, lactic acid, 2-chlorobenzoic acid, methanesulfonic acid, ethanesulfonic acid, p-toluene sulfonic acid and mixtures thereof.

A Bronsted acid can be an organic or an inorganic acid.

Examples of organic acids that can be used as Bronsted acid are fumaric acid, maleic acid, oxalic acid, citric acid, lactic acid, methanesulfonic acid, ethanesulfonic acid, p-toluene sulfonic acid and mixtures thereof. Preferred are methanesulfonic acid, ethanesulfonic acid and p-toluene sulfonic acid, in particular methanesulfonic acid and p-toluene sulfonic acid.

Examples of inorganic acids that can be used as Bronsted acid are hydrogen chloride (the corresponding acid is hydrochloric acid), hydrogen bromide, hydrogen iodide, nitric acid, sulfuric acid, sodium or potassium hydrogen sulfate, phosphoric acid and mixtures thereof.

In a preferred embodiment of the invention and/or embodiments thereof the acidic aqueous solution in step (iii) is a solution of an inorganic acid, preferably hydrogen chloride, hydrogen bromide, sulfuric acid, sodium or potassium hydrogen sulfate, phosphoric acid and mixtures thereof, more preferably hydrogen chloride, sodium or potassium hydrogen sulfate, phosphoric acid and mixtures thereof, in particular hydrogen chloride, potassium hydrogen sulfate, or phosphoric acid, especially potassium hydrogen sulfate.

In a preferred embodiment of the invention and/or embodiments thereof the acidic aqueous solution used in step (iii) has a pH value of −3 to 3.5, more preferably −2 to 3, even more preferably −1 to 2.5, in particular about 2.

Step (iii) of treating the precipitate from step (ii) with an acidic aqueous solution can be preferably be carried under cooling, preferably at a temperature of 5° C. to 20° C., more preferably about 10° C.

Further, the reaction of step (iii) can be preferably subjected to a mechanical movement such as stirring or ultrasonic treatment, in particular stirring.

In a preferred embodiment of the invention and/or embodiments thereof the duration of step (iii) can be between 5 minutes and 2 hours, preferably between 10 minutes and 1 hour, in particular about 30 minutes.

In step (iv) (5S)-4-[5-(3,5-dichlorophenyl)-5-(trifluoromethyl)-4H-isoxazol-3-yl]-2-methyl-benzoic acid is separated from the acidic aqueous solution of step (iii). Separating can comprise well known methods for separating a solid organic compound, in particular a solid organic acid, from an acidic aqueous solution. Separating can comprise methods such the ones as described in line with step (ii), i.e. the above-described decanting or pouring off the solution, optionally with a preceding centrifugation step, and filtration. Further, separating can be conducted via an extraction of the desired compound, (5S)-4-[5-(3,5-dichlorophenyl)-5-(trifluoromethyl)-4Hisoxazol-3-yl]-2-methyl-benzoic acid, from the acidic aqueous solution.

In a preferred embodiment of the invention and/or embodiments thereof in step (iv) the separation of (5S)-4-[5-(3,5-dichlorophenyl)-5-(trifluoromethyl)-4-Hisoxazol-3-yl]-2-methyl-benzoic acid from the acidic aqueous solution from step (iii) is carried out by an extraction with an organic solvent. Organic solvents are well known by those skilled in the art.

In step (iv) extraction can be preferably carried out in an aprotic organic solvent. Organic solvents suitable to be used in present step (iv) are for example toluene, benzene, xylene, ethyl acetate, hexane, heptane, octane, cyclic and acyclic alkylethers, chlorobenzene, cyclohexane, methylcyclohexane, dichloromethane, dichloroethane, trichloromethane, trichloroethane, tetrachloroethane, dimethoxyethane, diethoxyethane and combinations thereof. Preferred are ethyl acetate, toluene, dichloromethane and trichloromethane, in particular ethyl acetate and toluene, especially ethyl acetate.

The extraction preferably comprises adding organic solvent to the acidic aqueous solution from step (iii), mixing the two liquids, separating the phase with the organic solvent from the acidic aqueous solution. This procedure can preferably be repeated, preferably repeated two to four times. Subsequently the organic phases can be preferably combined and dried. Drying can be conducted with any known drying agent such as sodium sulfate or magnesium sulfate. After drying the drying agent can be separated from the organic phase, preferably by filtration.

Further step (iv) preferably comprises removing the organic solvent from the organic phase, preferably from the combined organic phase. Removing the organic solvent can preferably be conducted at a temperature of 23° C. to 50° C., preferably about 40° C. and/or at a reduced pressure of 1 kPa to 90 kPa, preferably about 10 kPa.

In a preferred embodiment of the invention and/or embodiments thereof the (5S)-4-[5-(3,5-dichlorophenyl)-5-(trifluoromethyl)-4Hisoxazol-3-yl]-2-methyl-benzoic acid from step (iv) has an enantiomeric excess (ee) of at least 75%, preferably of at least 80%, more preferably of at least 85%, in particular of at least 90%.

The enantiomeric excess (ee) is defined as the absolute difference between the mole fraction of each enantiomer and can expressed as a percent enantiomeric excess, which is calculated according to the equation:

$$ee=(|F_R-F_S|\times 100)\%$$

wherein
$F_R$ is the mole fraction of the (R)-enantiomer, and
$F_S$ is the mole fraction of the (S)-enantiomer The amount and thus the mole fraction of the corresponding enantiomer can be determined by the methods as known in the art, for example via the numerical value of the enantiomeric excess of the compound in question, via chiral column chromatography (chiral LC or SFC) or via NMR-spectroscopy in the presence of chiral shift reagents. In the present application chiral LC mole fraction of the corresponding enantiomer is determined by chiral LC (System: Agilent Technologies 1100 equipped with Agilent Technologies 1200 sampler. Phenomenex column (250 mm×4.6 mm) with Lux amylose-1 chiral phase (5 μm). Eluent: i-hexane: ethanol 75:25; isocratic run over 12 min. Flow: 1 mL/min. Temperature of column oven: 35° C. UV-detection at 220, 254, 265 and 280 nm). Other possibilities are transformation of the (S)-IOBA with chiral amines or alcohols into diastereoisomeric amides or esters and determination of the ee % via LC.

In a preferred embodiment of the invention and/or embodiments thereof the present method further comprises step (v) of recrystallizing the product from step (iv), (5S)-4-[5-(3,5-dichlorophenyl)-5-(trifluoromethyl)-4H-isoxazol-3-yl]-2-methyl-benzoic acid. Recrystallizing or recrystallization is a process in which the desired compound and optional impurities are dissolved in an appropriate solvent. Subsequently the desired compound precipitates (recrystallizes), while the optional impurities remain in the solvent.

The compound to be recrystallized is preferably dissolved in the solvent, preferably in the solvent at its boiling temperature, in an amount just about enough to completely dissolve the compound. It is further preferred that subsequently the temperature of the solvent is cooled such that a precipitate of the desired product can be formed. Separating the desired compound, (5S)-4-[5-(3,5-dichlorophenyl)-5-(trifluoromethyl)-4-H-isoxazol-3-yl]-2-methyl-benzoic can be done as described above for example with regard to step (ii).

Suitable organic solvents for recrystallisation are for example toluene, benzene, xylene, ethyl acetate, hexane, cyclic and acyclic alkylethers, chlorobenzene, cyclohexane, methylcyclohexane and combinations thereof. Preferred are acyclic alkylethers, toluene and ethyl acetate.

In a preferred embodiment of the invention and/or embodiments thereof of the present method (5S)-4-[5-(3,5-dichlorophenyl)-5-(trifluoromethyl)-4H-isoxazol-3-yl]-2-methyl-benzoic acid is further reacted with a compound according to Formula (4)

Formula (4)

to give (5S)-4-[5-(3,5-dichlorophenyl)-5-(trifluoromethyl)-4H-isoxazol-3-yl]-N-[2-oxo-2-(2,2,2-trifluoroethylamino)ethyl]-2-methyl-benzamide according to Formula (3)

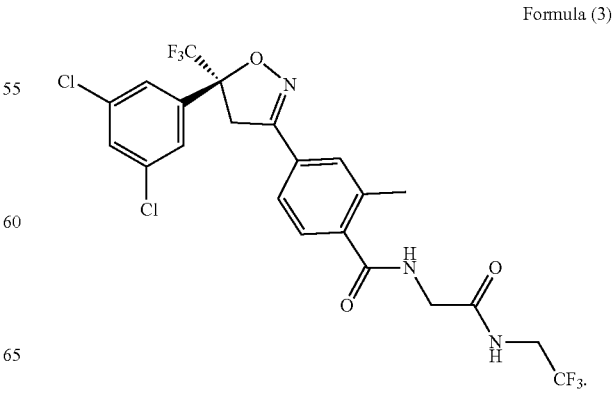

Formula (3)

Preferably (5S)-4-[5-(3,5-dichlorophenyl)-5-(trifluoromethyl)-4H-isoxazol-3-yl]-2-methyl-benzoic acid and the amine according to Formula (4) can be submitted to form the corresponding amide group in an organic solvent in the presence of a coupling agent. A coupling agent is preferably a substance generally facilitating the formation of an ester or an amide. The coupling agent reacts with a carboxy group by forming a reactive intermediate which is subsequently further reacted with an alcohol or an amine to form the final product, i.e. an ester or an amide. Suitable coupling agents can be for example N,N'-dicyclohexylcarbodiimide (DCC), 1-ethyl-3-(3-dimethylaminopropyl) carbodiimide (EDC) or carbonyldiimidazole (CDI).

A suitable organic solvent can for example be dioxane, tetrahydrofuran and DMF.

Alternatively (5S)-4-[5-(3,5-dichlorophenyl)-5-(trifluoromethyl)-4H-isoxazol-3-yl]-2-methyl-benzoic acid can be preferably reacted with thionylchloride or oxalylchloride, preferably thionylchloride, to form the corresponding acid chloride. Subsequently the corresponding acid chloride can be submitted to a reaction with the amine according to Formula (4) preferably in an organic solvent, such as dioxane, tetrahydrofuran, chloroform or dichloromethane. Further, the reaction of the acid chloride with amine according to Formula (4) is preferably carried out in the presence of an auxiliary alkaline compound. Suitable alkaline compounds are for example pyridine and amines, such as triethylamine and diisopropylethylamine, preferably diisopropylethylamine.

A further subject of the present invention is a method for preparing (5S)-4-[5-(3,5-dichlorophenyl)-5-(trifluoromethyl)-4H-isoxazol-3-yl]-2-methyl-benzoic acid according to Formula (1a)

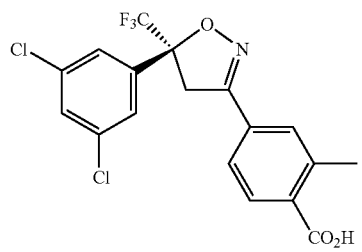

Formula (1a)

from (5RS)-4-[5-(3,5-dichlorophenyl)-5-(trifluoromethyl)-4H-isoxazol-3-yl]-2-methyl-benzoic acid according to Formula (1)

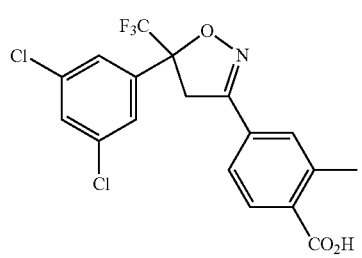

Formula (1)

comprising the steps of:
(i) reacting (5RS)-4-[5-(3,5-dichlorophenyl)-5-(trifluoromethyl)-4H-isoxazol-3-yl]-2-methyl-benzoic acid with a compound of Formula (2A), (2B) or (2C)

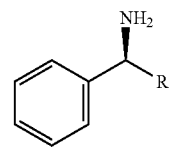

Formula (2A)

wherein R is an alkyl with 1 or 2 carbon atoms,

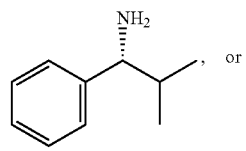

Formula (2B)

, or

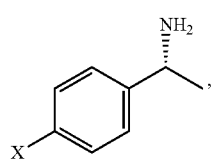

Formula (2C)

, wherein X is Cl or Br,
in an organic solvent selected from methyl tert-butyl ether, cyclopentyl methyl ether, tetrahydrofuran, dioxane, chlorobenzene, toluene, m-xylene, mesitylene, ethyl acetate, butyl acetate, triethylamine, trichloromethane, 1,2-dichloroethane to form a precipitate and a supernatant solution (ii) separating the precipitate from step (i) from the supernatant solution (iii) treating the precipitate from step (ii) with acidic aqueous solution, and (iv) separating (5S)-4-[5-(3,5-dichlorophenyl)-5-(trifluoromethyl)-4H-isoxazol-3-yl]-2-methyl-benzoic acid from the acidic aqueous solution of step (iii), under the proviso that, when R is methyl, the solvent in step (i) is not ethyl acetate.

As far as the preferred embodiments are concerned, the same applies as described above.

A further subject of the present invention is a method for preparing (5S)-4-[5-(3,5-dichlorophenyl)-5-(trifluoromethyl)-4H-isoxazol-3-yl]-2-methyl-benzoic acid according to Formula (1a)

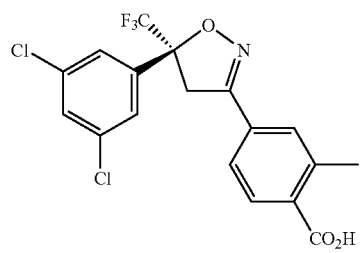

Formula (1a)

from (5RS)-4-[5-(3,5-dichlorophenyl)-5-(trifluoromethyl)-4H-isoxazol-3-yl]-2-methyl-benzoic acid according to Formula (1)

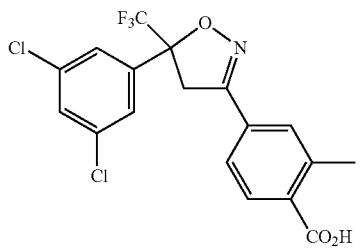

Formula (1)

comprising the steps of:
(i) reacting (5RS)-4-[5-(3,5-dichlorophenyl)-5-(trifluoromethyl)-4H-isoxazol-3-yl]-2-methyl-benzoic acid with a compound of Formula (2A), (2B) or (2C)

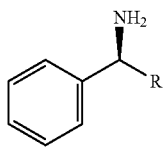

Formula (2A)

wherein R is an alkyl with 1 or 2 carbon atoms,

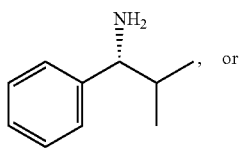

Formula (2B)

or

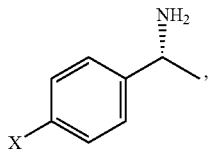

Formula (2C)

wherein X is Cl or Br,
in a first organic solvent having a polarity $E_T(30)$ between 130 and 175 kJ/mol to form a precipitate and a supernatant solution
(ii) separating the precipitate from step (i) from the supernatant solution
(iii) optionally, treating the precipitate from step (ii) with acidic aqueous solution, and
(iv) optionally separating (5S)-4-[5-(3,5-dichlorophenyl)-5-(trifluoromethyl)-4H-isoxazol-3-yl]-2-methyl-benzoic acid from the acidic aqueous solution of step (iii)
(v) optionally, recrystallizing the product from step (iv), (5S)-4-[5-(3,5-dichlorophenyl)-5-(trifluoromethyl)-4H-¬ isoxazol-3-yl]-2- methyl-benzoic acid
(vi) reacting the supernatant solution with an alkaline compound in a second organic solvent, under the proviso that, when R is methyl, the solvent in step (i) is not ethyl acetate.

After the precipitation of (5S)-4-[5-(3,5-dichlorophenyl)-5-(trifluoromethyl)-4H-isoxazol-3-yl]¬-2-methyl-benzoic acid (S-IOBA) the supernatant will be a mixture of (R)-4-[5-(3,5-dichlorophenyl)-5-(trifluoromethyl)-4H-isoxazol-3-yl)]-2-methyl-benzoic acid (R-IOBA) according to Formula (1b) and (S)-4-[5-(3,5-dichlorophenyl)-5-(trifluoromethyl)-4H-isoxazol-3-yl)]-2-methyl-benzoic acid (S-IOBA) according to Formula (1a).

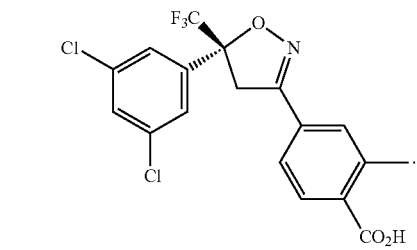

Formula (1b)

In most cases, the supernatant will be enriched in (R)-4-[5-(3,5-dichlorophenyl)-5-(trifluoromethyl)-4H-isoxazol-3-yl)]-2-methyl-benzoic acid (R-IOBA).

In step (vi) of the method according to the invention and/or any embodiment thereof the mixture containing (R)-IOBA according to Formula (1a) and (S)-IOBA according to Formula (1b) is reacted with an alkaline compound in an organic solvent. This reaction will racemize the mixture and will shift the enantiomeric excess of (R)-IOBA to a lower value. Racemizing is not strictly considered as shifting the enantiomeric value to 0, which is the literal meaning of a racemate.

An alkaline compound can be an organic or an inorganic alkaline compound.

Examples of organic alkaline compounds are diisopropylethylamine (DIPEA), 1,8-diazabicyclo[5.4.0]undec-7-ene (DBU), 1,5-diazabicyclo[4.3.0]non-5-e and 2-tert-btuy-imino-2-dietalamino-1,3-dimethylperhydro-1,3,2-diazaphosphorine and mixtures thereof.

In a preferred embodiment of the invention and/or embodiments thereof the alkaline compound in step (i) is an inorganic compound.

Examples of suitable inorganic alkaline compounds are alkali or earth alkali phosphates, alkali or earth alkali carbonates, alkali or earth alkali hydrogen carbonates, alkali or earth alkali hydroxides, alkali or earth alkali oxides or mixtures thereof.

In a preferred embodiment of the invention and/or embodiments thereof the alkaline compound in step (vi) can be selected from the group consisting of lithium oxide, sodium oxide, potassium oxide, cesium oxide, lithium hydroxide, sodium hydroxide, potassium hydroxide, cesium hydroxide, calcium hydroxide barium hydroxide, magnesium oxide, calcium oxide, barium oxide, cesium carbonate and mixtures thereof. Preferred are sodium hydroxide, potassium hydroxide, cesium hydroxide, calcium hydroxide, barium hydroxide, barium oxide and mixtures thereof.

In a preferred embodiment of the invention and/or embodiments thereof the alkaline compound in step (vi) can be selected from the group consisting of sodium hydroxide, potassium hydroxide, cesium hydroxide and mixtures thereof.

Further alkaline compound suitable to be used in step (vi) are alkali or earth alkali alkoholates. Suitable examples are sodium methanolate, potassium methanolate, sodium ethanolate, potassium ethanolate, sodium tert-butylate and potassium ter-butylate and mixtures thereof.

Step (vi) of the present method is carried out in a second organic solvent.

Suitable second organic solvents are for example water, alcohols such as propanol, cyclic ethers such as tetrahydrofuran and dioxane, aliphatic esters such as ethyl acetate, unsubstituted or substituted arenes such as benzene and toluene.

In a preferred embodiment of the invention and/or embodiments thereof the second organic solvent is selected from the group consisting of water, alcohol with 1 to 5 carbons atoms, tetrahydrofuran, dioxane, toluene, ethyl acetate and mixtures thereof, more preferred from the group consisting of water, alcohol with 2 to 5 carbons atoms, dioxane, toluene and mixtures thereof.

In a preferred embodiment of the invention and/or embodiments thereof the second organic solvent in step (vi) is an alcohol with 1 to 5 carbon atoms. The alcohol is preferably a mono alcohol, i.e. the organic solvent carries just one hydroxy group. It is further preferred that the second organic solvent just carries the hydroxy functional group. In other words, the alcohol does not carry any other functional group apart from the (one) hydroxy group. Further, the alcohol with 1 to 5 carbon atoms used as second organic solvent just contains hydrogen, oxygen and carbon atom(s). Suitably the alcohol is not further substituted.

Examples of alcohols with 1 to 5 carbon atoms used as organic solvent are methanol, ethanol, 1-propanol, 2-propanol, cyclopropyl alcohol, 1-butanol, 2-butanol, cyclobutanol, 2-methyl-1-propanol, 2-methyl-2-propanol, 1-pentanol, 2-pentanol, 3-pentanol, cyclopentanol, 2-methyl-1-butanol, 3-methyl-1-butanol, 3-methyl-2-butanol, 2-methyl-2-butanol, 2,2-dimethyl-1-propanol and mixtures thereof.

In a preferred embodiment of the invention and/or embodiments thereof the second organic solvent is an alcohol with 1 to 5 carbon atoms selected from the group consisting of ethanol, 1-propanol, 2-propanol, 1-butanol, 2-butanol, 2-methyl-1-propanol, 1-pentanol, 2-pentanol, 3-pentanol and mixtures thereof. More preferably the second organic solvent is an alcohol with 2 to 5 carbon atoms selected from the group consisting ethanol, 1-propanol, 2 propanol, 1-butanol, 1-pentanol and mixtures thereof.

In a particularly preferred embodiment of the invention and/or embodiments thereof the second organic solvent in step (vi) is the same as the first organic solvent having a polarity ET(30) between 130 and 175 kJ/mol of step (i).

In a particularly preferred embodiment of the invention and/or embodiments thereof the second organic solvent in step (vi) is ethanol.

In a preferred embodiment of the invention and/or embodiments thereof in step (vi) the second organic solvent is ethanol and the alkaline compound is sodium hydroxide.

In a preferred embodiment of the invention and/or embodiments thereof in step (vi) the second organic solvent is ethanol and the alkaline compound is potassium hydroxide.

In a preferred embodiment of the invention and/or embodiments thereof in step (vi) the second organic solvent is ethanol and the alkaline compound is cesium hydroxide.

In a preferred embodiment of the invention and/or embodiments thereof in step (vi) the second organic solvent is ethanol and the alkaline compound is calcium hydroxide.

In a preferred embodiment of the invention and/or embodiments thereof in step (vi) the second organic solvent is ethanol and the alkaline compound is barium hydroxide.

In a preferred embodiment of the invention and/or embodiments thereof in step (vi) the second organic solvent is ethanol and the alkaline compound is barium oxide.

In a particularly preferred embodiment of the invention and/or embodiments thereof the second organic solvent in step (vi) is 1-propanol.

In a preferred embodiment of the invention and/or embodiments thereof in step (vi) the second organic solvent is 1-propanol and the alkaline compound is sodium hydroxide.

In a preferred embodiment of the invention and/or embodiments thereof in step (vi) the second organic solvent is 1-propanol and the alkaline compound is potassium hydroxide.

In a preferred embodiment of the invention and/or embodiments thereof in step (vi) the second organic solvent is 1-propanol and the alkaline compound is cesium hydroxide.

In a preferred embodiment of the invention and/or embodiments thereof in step (vi) the second organic solvent is 1-propanol and the alkaline compound is calcium hydroxide.

In a preferred embodiment of the invention and/or embodiments thereof in step (vi) the second organic solvent is 1-propanol and the alkaline compound is barium hydroxide.

In a preferred embodiment of the invention and/or embodiments thereof in step (vi) the second organic solvent is 1-propanol and the alkaline compound is barium oxide.

In a particularly preferred embodiment of the invention and/or embodiments thereof the second organic solvent in step (vi) is 2-propanol.

In a particularly preferred embodiment of the invention and/or embodiments thereof in step (vi) the second organic solvent is 2-propanol and the alkaline compound is sodium hydroxide.

In a particularly preferred embodiment of the invention and/or embodiments thereof in step (vi) the second organic solvent is 2-propanol and the alkaline compound is potassium hydroxide.

In a particularly preferred embodiment of the invention and/or embodiments thereof in step (vi) the second organic solvent is 2-propanol and the alkaline compound is cesium hydroxide.

In a particularly preferred embodiment of the invention and/or embodiments thereof in step (vi) the second organic solvent is 2-propanol and the alkaline compound is calcium hydroxide.

In a particularly preferred embodiment of the invention and/or embodiments thereof in step (vi) the second organic solvent is 2-propanol and the alkaline compound is barium hydroxide.

In a particularly preferred embodiment of the invention and/or embodiments thereof in step (vi) the second organic solvent is 2-propanol and the alkaline compound is barium oxide.

In a particularly preferred embodiment of the invention and/or embodiments thereof the second organic solvent in step (vi) is toluene.

In a particularly preferred embodiment of the invention and/or embodiments thereof in step (vi) the second organic solvent is toluene and the alkaline compound is sodium oxide.

In a particularly preferred embodiment of the invention and/or embodiments thereof in step (vi) the second organic solvent is toluene and the alkaline compound is potassium oxide.

In a particularly preferred embodiment of the invention and/or embodiments thereof in step (vi) the second organic solvent is toluene and the alkaline compound is cesium oxide.

In a preferred embodiment of the invention and/or embodiments thereof the molar ratio of the mixture containing (R)-IOBA according to Formula (1b) and (S)-IOBA according to Formula (1a) to the alkaline compound is 1:1 to 1:10, more preferably 1:2 to 1:8, in particular 1:3 to 1:6, especially about 1:4.5

In a preferred embodiment of the invention and/or embodiments thereof step (vi) is carried out at an elevated temperature. An elevated temperature is a temperature from 23° C. (room temperature) to the boiling temperature of the organic solvent. In a preferred embodiment of the invention and/or embodiments thereof step (i) is carried out at the boiling temperature of the organic solvent. All temperatures as indicated herein and relating to boiling temperatures or boiling points relate to temperatures measured at normal pressure of 101 kPa.

Further, the reaction of step (vi) can be preferably subjected to a mechanical movement such as stirring or ultrasonic treatment.

In a preferred embodiment of the invention and/or embodiments thereof the duration of step (vi) can be between 30 minutes and 48 hours, preferably between 2 hour and 36 hours, in particular between 4 hours and 24 hours.

In a preferred embodiment of the invention and/or embodiments thereof step (vi) is carried out in the absence of phase transfer catalysts. A phase transfer catalyst can be regarded as a substance that facilitates the migration of a reactant from one phase into another phase where reaction occurs. A phase transfer catalyst can also be regarded as a heterogenous catalyst. A phase transfer catalyst is often difficult to remove from a reaction mixture and/or a desired product and hence any reaction which can be carried out without phase transfer catalyst is advantageous.

The resulting racemic mixture obtained after step (vi) can then be used again in any method according to the invention and/or any embodiments thereof in step (i). In this way the yield of (5S)-4-[5-(3,5-dichlorophenyl)-5-(trifluoromethyl)-4H-isoxazol-3-yl]¬-2-methyl-benzoic acid can be enhanced. In addition, step (vi) enables the recycling of the unwanted product (5R)-4-[5-(3,5-dichlorophenyl)-5-(trifluoromethyl)-4H-isoxazol-3-yl]¬-2-methyl-benzoic acid.

Features of the invention have been described in embodiments in the present application; however, for the sake of brevity not all combinations of the features are literally described. Combinations of features as described above are, however, expressly considered to be part of the invention.

The invention will now be further described by the following, non-limiting, examples.

The yields are calculated on the fraction of (S)-IOBA within the starting material.

This amount of (S)-IOBA represents 100% yield:

EXPERIMENTAL PART

I. Prior Art Rework

I.1 Example 1 of JP 05679102

(5RS)-4-[5-(3,5-dichlorophenyl)-5-(trifluoromethyl)-4H-isoxazol-3-yl]-2-methyl-benzoic acid (2.09 g; 5.0 mmol), toluene (10 g) and ethyl acetate (5 g) were charged and stirred at 54° C. Thereto, (L)-(−)-α-phenylethylamine ((S)-1-phenylethyl amine; 0.304 g; 2.5 mmol) was added, wherein precipitation started within seconds. The reaction mixture was cooled to 4° C. within 1 hour under stirring. The resulting solid was collected by filtration under reduced pressure. After washing with toluene/ethyl acetate 5:1 (5 mL) the diastereomeric salt of (5S)-4-[5-(3,5-dichlorophenyl)-5-(tri-fluoromethyl)-4H-isoxazol-3-yl]-2-methyl-benzoic acid and (L)-(−)-α-phenylethylamine 1:1 was obtained as white solid.

Yield: 1.12 g

Enantiomeric excess (ee): 76%

I.2 Example 4 of JP 05679102

Ethyl acetate (10 mL) and toluene (15 mL) were added to the diastereomeric salt of (5S)-4-[5-(3,5-dichlorophenyl)-5-(trifluoromethyl)-4H-isoxazol-3-yl]-2-methyl-benzoic acid and (L)-(−)-α-phenylethylamine 1:1 (0.5 g) as obtained from above Example 1 of JP 05679102. Hereto, diluted hydrochloric acid (purified water (3 mL) and 35% hydrochloric acid (0.53 g)) were added and the mixture warmed to 40° C. for 5 minutes. The phases were separated, and the organic phase was washed with diluted hydrochloric acid (purified water (3 mL) and 35% hydrochloric acid (0.53 g)) and subsequently with purified water (3 mL). Then, the organic solvent was distilled under reduced pressure from the organic phase and the residue was dried under reduced pressure to obtain an amorphous substance, 4-[5-(3,5-dichlorophenyl)-5-(trifluoromethyl)-4H-isoxazol-3-yl]-2-methyl-benzoic acid.

Yield: 0.42 g

Enantiomeric excess (ee) above: 77%

Conclusion:

In Example 1 of JP 05679102 the enantiomeric excess of the diastereomeric salt of (5S)-4-[5-(3,5-dichlorophenyl)-5-(trifluoromethyl)-4H-isoxazol-3-yl]-2-methyl-benzoic acid and (L)-(−)-α-phenylethylamine 1:1 is just 76% and, thus, significantly lower than cited in the prior art (90% ee). The same applies to the enantiomeric excess of the (5S)-4-[5-(3,5-dichlorophenyl)-5-(trifluoromethyl)-4H-isoxazol-3-yl]-2-methyl-benzoic acid as obtained in Example 4 of JP 05679102 (80% ee).

As far as the yields obtained in both Examples are concerned, these approximately correspond to the ones from the prior art.

I.3 Example 2 of WO 2014/090918

Example 2 of WO 2014/090918 was reworked, wherein racemic IOBA instead of the isoxazoline thiophene carboxylic acid (IOTA) according to WO 2014/090918 and smaller amounts were used.

A ternary solvent mixture consisting of 2-butanol (4.631 mL), acetonitrile (18.881 mL) and water (0.987 mL) was prepared. (5RS)-4-[5-(3,5-dichlorophenyl)-5-(trifluoromethyl)-4H-isoxazol-3yl]-2-methyl-benzoic acid (2 g, 4.78 mmol) were dissolved under stirring. A solution of (R)-(+)-1-(4-methylphenyl)ethylamine (0.358 mL, 2.433 mmol) in a ternary mixture consisting of 2-butanol (0.515 mL, 5.63 mmol), acetonitrile (2.110 mL, 40.6 mmol) and water (0.110 mL, 6.11 mmol) was prepared and was added to the solution of IOBA. The mixture was heated towards 60-65° C. under stirring for 120 min. The stirrer was turned off and the solution cooled down to room temperature overnight. The formation of crystals was not observed.

The solvent was evaporated, and the residue was dried under reduced pressure. The material was suspended in acetonitrile (20 mL) and heated towards 70° C. 2-butanol (4 mL) and water (3.4 mL) were added consecutively while heating the reaction mixture to 70° C. A clear solution resulted after the complete portion of water had been added. The mixture cooled down and rested for two days.

A floor of solid material was formed. The solid was suspended under stirring in the supernatant and additional material precipitated. After the precipitation of solid had been stopped, the material was collected, washed with acetonitrile/water 9:1 and dried under reduced pressure overnight. The weight of the solid was 610 mg.

The supernatant as well as a sample of the solid was analyzed by chiral LC after acidic workup with potassium hydrogen sulfate and extraction in ethyl acetate. The chiral LC analysis revealed that equal amounts of (S)- and (R)-IOBA were present in both samples. The conditions applied in WO 2014/090918 for the separation of the IOTA enantiomers are not useful in the case of IOBA for the genaration of (S)-IOBA.

II. Screening Examples According to the Present Invention (Smaller Scale)

II.1 General Procedure for the Synthesis of (5S)-4-[5-(3,5-dichlorophenyl)-5-(trifluoromethyl)-4-Hisoxazol-3-yl]-2-methyl-benzoic acid Step (i)
A solution of (5RS)-4-[5-(3,5-dichlorophenyl)-5-(trifluoromethyl)-4H-isoxazol-3-yl]-2-methyl-benzoic acid (92 mg) in 1.1 mL of the corresponding solvents A,-M was prepared. The mixture was stirred and gently warmed, where necessary, until the solid had been dissolved. A reaction block in which 13×2 vials (13 rows, 2 columns) were charged with equal aliquots of the solutions (500 μL) A-M; one type of solution per row. The corresponding neat chiral bases 1 and 2 (0.6 eq) were added (one base per column) and the mixture was stirred under heating to 75° C. for 10 min. Afterwards the reaction mixtures cooled down under stirring to room temperature.

Step (ii)
From the reaction mixture of step (i) containing the precipitate the supernatant solution was separated by filtration or centrifugation. The collected colourless solids were washed with the corresponding solvent and the suspensions were filtrated or centrifuged again. Subsequently the obtained solids were dried overnight.

Step (iii)
The dried solid material was suspended in ethyl acetate, the resulting suspension was charged with water and potassium hydrogen sulfate, and a bi-layered system was obtained, wherein the aqueous phase had a pH of about 1. The two phases were mixed until all solid material had been dissolved.

Step (iv)
The organic (ethyl acetate) phase of the bi-layered system was separated. The aqueous phase of the bi-layered system was extracted twice with ethyl acetate. The organic phases were combined, and the solvent was evaporated in order to obtain a colorless material.

The resulting (5S)-4-[5-(3,5-dichlorophenyl)-5-(trifluoromethyl)-4H-isoxazol-3-yl]-2-methyl-benzoic acid has the following enantiomeric excess

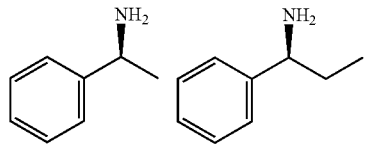

| % ee | 1 | 2 |
|---|---|---|
| A (dioxane) | 91 | 88 |
| B* (tetrahydrofuran) | n.d. | 68 |
| C (toluene) | 76 | 89 |
| D (ethyl acetate) | 91 | 94 |
| E (methyl tert-butyl ether) | 44 | 82 |
| F (cyclopentyl methyl ether) | 32 | 90 |
| G (chlorobenzene) | 90 | 93 |
| H (m-xylene) | 34 | 90 |
| I (mesitylene) | 39 | 89 |
| J (butyl acetate) | 86 | 92 |
| K (triethylamine) | 91 | 93 |
| L (trichloromethane) | 80 | 76 |
| M (1,2-dichloroethane) | 88 | 91 |

B* 3 eq. of the chiral base were applied calculated on the amount of the racemic (IOBA)

As can be seen, the resulting (5S)-4-[5-(3,5-dichlorophenyl)-5-(trifluoromethyl)-4H-isoxazol-3yl]-2-methyl-benzoic acid shows an advantageous or a significantly higher enantiomeric excess than the prior art (JP 05679102), in particular when (R)-1-phenyl-1-propylamine was used as chiral base.

III. Working Examples (Lager Scale)

III.1

A flask equipped with a condenser and a thermometer was charged with 2-propanol (12.5 mL) and water (0.85 mL). Solid potassium hydroxide (0.671 g, 11.96 mmol) was dissolved in the solvent and (5R)-4-(5-(3,5-dichlorophenyl)-5-(trifluoromethyl)-4H-isoxazol-3-yl)-2-methylbenzoic acid with 87.2% ee (1 g, 2.391 mmol) was added at 23° C. (room temperature). The mixture was heated to 80° C.

A 50 μl sample was taken after 1 hour, 2 hours and 16 hours, respectively, for determining the degree of racemisation. Each of the samples was treated as follows: It was quenched with $KHSO_4$-solution (1 mL, 2.3 M) and extracted twice with ethyl acetate (once with 2 mL and once with 1 mL). The combined organic phases were concentrated under reduced pressure. The residue was dried under oil-pump vacuum and dissolved in a mixture of i-hexane ethanol 1:1 (1 mL).

The resulting (R)-IOBA has an enantiomeric excess of 84.8% after one hour, of 84.5% after two hours and of 64% after 16 hours.

III.2

A flask equipped with a condenser and a thermometer was charged with 2-propanol (6.67 mL) and (5R)-4-(5-(3,5-dichlorophenyl)-5-(trifluoromethyl)-4H-isoxazol-3-yl)-2-methylbenzoic acid with 86.4% ee (1 g, 2.391 mmol) was dissolved. Sodium hydroxide (0.393 g, 9.83 mmol) micro pearls were added at 40° C. and the mixture was heated to reflux, whereby a yellow-coloured suspension resulted.

A 50 μL sample was taken after 2 hours, 4 hours and 20 hours, respectively, for determining the degree of racemisation. Each of the samples was treated as described in Example 1.

The resulting (R)-IOBA has an enantiomeric excess of 62.4% after two hours, of 35.0% after four hours and of 31.8% after 20 hours.

III.3

A solution of (5R)-4-(5-(3,5-dichlorophenyl)-5-(trifluoromethyl)-4H-isoxazol-3-yl)-2-methylbenzoic acid with >99% ee (50 mg, 0.120 mmol) in 2-propanol (299 μL) was incubated with a 2-propanol solution of potassium hydroxide (20.38 μL, 0.359 mmol) in a 1 mL conical vial. The mixture was heated to 90° C. overnight.

A sample of 100 μL of the reaction mixture was concentrated to a solid, diluted with 2 mL aqueous $KHSO_4$ (15%) and extracted with 1 to 2 mL ethyl acetate. The organic phase was separated and concentrated. The oil was dried under reduced vacuum and dissolved in i-hexane:ethanol 1:1 (1 mL). From this solution 250 μL were diluted with i-hexane:ethanol 1:1 (1 mL) and analysed via chiral LC-DAD. The resulting (R)-IOBA had an enantiomeric excess of 56.47%.

III.4

A solution of (R)-4-(5-(3,5-dichlorophenyl)-5-(trifluoromethyl)-4,5-dihydroisoxazol-3-yl)-2-methylbenzoic acid with >99% ee (50 mg, 0.120 mmol) in 2-Propanol (299 μL) was incubated with a 2-propanol solution of cesium hydroxide (66.8 μL, 0.359 mmol) in a 1 mL conical vial. The mixture was heated to 90° C. overnight.

A sample of 100 μL of the reaction mixture was concentrated to a solid, diluted with 2 mL aqueous $KHSO_4$ (15%) and extracted with 1-2 mL ethyl acetate. The organic phase was separated and concentrated. The oil was dried under reduced vacuum and dissolved in i-hexane:ethanol 1:1 (1 mL). From this solution 250 μL were diluted with i-hexane:ethanol 1:1 (1 mL) and analysed via chiral LC-DAD. The resulting (R)-IOBA has an enantiomeric excess of 27.76%.

III.5

A flask was equipped with a condenser and a thermometer. The flask was charged with 2-propanol (6.67 ml), powdered potassium hydroxide (0.671 g, 11.96 mmol) was dissolved in the solvent and (5R)-4-(5-(3,5-dichlorophenyl)-5-(trifluoromethyl)-4H-isoxazol-3-yl)-2-methylbenzoic acid with 87.2% ee (1 g, 2.391 mmol) was added at 40° C. The mixture was heated to reflux. A clear orange solution was formed. After a while, a yellow-coloured solid material precipitated. The suspension was further heated to reflux. After 2 h, a 50 μL-sample of the suspension was worked up as described in Example 5. The resulting (R)-IOBA had an enantiomeric excess of 0.8%.

As can be seen from Examples 1 to 5, the excess of (R)-IOBA contained in the resulting product is reduced. Thus, it can be concluded that the molar ratio of (S)-IOBA is increased by racemising the starting mixture.

III.6

A 50 mL three-necked flask was charged with (5RS)-4-(5-(3,5-dichlorophenyl)-5-(tri-fluoromethyl)-4H-isoxazol-3yl]-2-methyl-benzoic acid (2.323 g, 5.0 mmol) and cyclopentyl methyl ether (12.5 mL). The reaction mixture was stirred at 23° C. (S)-1-phenylpropan-1-amine (0.363 mL, 2.50 mmol) was added to the yellow-coloured solution and a white solid started to precipitate. The stirred suspension was heated to 80° C. within 20 minutes and then kept at that temperature for another 20 minutes. Heating was stopped and within two hours the suspension slowly cooled down to 40° C. The heating bath was removed and the suspension was stirred at room temperature over night.

The suspension was filtrated (frit no. 4) and the filtercake was washed with cyclopentyl methyl ether (6 mL) twice and subsequently dried in vacuo at 60° C.

The obtained ammonium salt was suspended in ethyl acetate (30 mL) and washed with aqueous potassium hydrogen sulphate (15 wt %, 20 mL) and the organic phase was separated. The aqueous phase was extracted with ethyl acetate (20 mL) and the combined organic phases were washed with brine (10 mL) and dried over $MgSO_4$. The drying agent was filtered off and the solvent was concentrated under reduced pressure. Finally, the residue was dried in high vacuo to obtain (S)-IOBA with an enantiomeric excess of 95%.

Yield 0.91 g (84%).

The invention claimed is:

1. A Method for preparing (S) 4-[5-(3,5-dichlorophenyl)-5-(trifluoromethyl)-4Hisoxazol-3yl)]-2-methyl-benzoic acid according to Formula (1a)

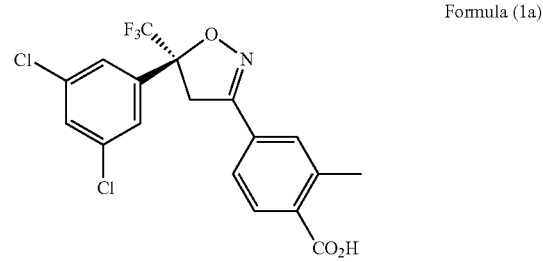

Formula (1a)

from (RS) 4-[5-(3,5-dichlorophenyl)-5-(trifluoromethyl)-4H-isoxazol-3-yl)]-2-methyl-benzoic acid according to Formula (1)

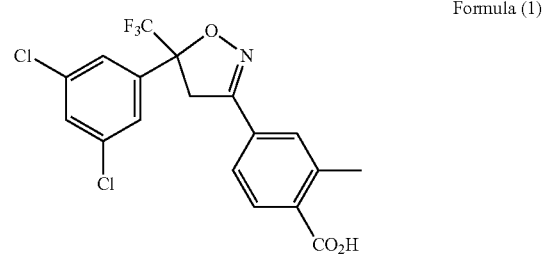 [SMILES: Cc1cc(C2=NOC(c3cc(Cl)cc(Cl)c3)(C(F)(F)F)C2)ccc1C(=O)O]

Formula (1)

comprising the steps of:
(i) reacting (RS) 4-[5-(3,5-dichlorophenyl)-5-(trifluoromethyl)-4H-isoxazol-3-yl)]-2-methyl-benzoic acid with a compound of Formula (2A), (2B) or (2C)

Formula (2A)

wherein R is an alkyl with 1 or 2 carbon atoms,

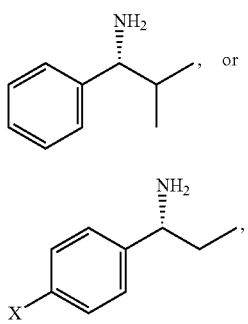

wherein X is Cl or Br,
in an organic solvent having a polarity $E_T(30)$ between 130 and 175 kJ/mol to form a precipitate and a supernatant solution
(ii) separating the precipitate from step (i) from the supernatant solution
(iii) treating the precipitate from step (ii) with acidic aqueous solution, and
(iv) separating (S)-4-[5-(3,5-dichlorophenyl)-5-(trifluoromethyl)-4H-isoxazol-3-yl)]-2-methyl-benzoic acid from the acidic aqueous solution of step (iii), under the proviso that, when R is methyl, the solvent in step (i) is not ethyl acetate.

2. The Method according to claim 1, wherein (5RS)-4-[5-(3,5-dichlorophenyl)-5-(trifluoromethyl)-4H-isoxazol-3-yl]-2-methyl-benzoic acid is reacted in step (i) with a compound of Formula (2A), (2B) or (2C) in a molar ratio of between 1:0.4 and 1:5.

3. The Method according to claim 1, wherein in step (i) the solvent is selected from methyl tert-butyl ether, cyclopentyl methyl ether, tetrahydrofuran, dioxane, chlorobenzene, toluene, m-xylene, mesitylene, ethyl acetate, butyl acetate, triethylamine, trichloromethane, 1,2-dichloroethane and mixtures thereof.

4. The Method according to claim 1, wherein in step (i) R of Formula (2A) is methyl and the solvent is methyl tert-butyl ether, or R of Formula (2A) is methyl and the solvent is cyclopentyl methyl ether, or R of Formula (2A) is methyl and the solvent is tetrahydrofuran, or R of Formula (2A) is methyl and the solvent is dioxane, or R of Formula (2A) is methyl and the solvent is chlorobenzene, or R of Formula (2A) is methyl and the solvent is toluene, or R of Formula (2A) is methyl and the solvent is m-xylene, or R of Formula (2A) is methyl and the solvent is mesitylene, or R of Formula (2A) is methyl and the solvent is butyl acetate, R of Formula (2A) is methyl and the solvent is triethylamine, or R of Formula (2A) is methyl and the solvent is trichloromethane, or R of Formula (2A) is methyl and the solvent is 1,2 dichloroethane.

5. The Method according to claim 1, wherein in step (i) R of Formula (2A) is ethyl and the solvent is methyl tert-butyl ether, or R of Formula (2A) is ethyl and the solvent is cyclopentyl methyl ether, or R of Formula (2A) is ethyl and the solvent is tetrahydrofuran, R of Formula (2A) is ethyl and the solvent is dioxane, or R of Formula (2A) is ethyl and the solvent is chlorobenzene R of Formula (2A) is ethyl and the solvent is toluene, or R of Formula (2A) is ethyl and the solvent is m-xylene, or R of Formula (2A) is ethyl and the solvent is mesitylene, or R of Formula (2A) is ethyl and the solvent is ethyl acetate, or R of Formula (2A) is ethyl and the solvent is butyl acetate, R of Formula (2A) is ethyl and the solvent is triethylamine, or R of Formula (2A) is ethyl and the solvent is trichloromethane, or R of Formula (2A) is ethyl and the solvent is 1,2 dichloroethane.

6. The Method according to claim 1, wherein in step (i) the compound is compound of Formula (2B) and the solvent is tetrahydrofuran, the compound is compound of Formula (2B) and the solvent is dioxane, the compound of Formula (2B) and the solvent is toluene, or the compound of Formula (2B) and the solvent is ethyl acetate, or the compound of Formula (2B) and the solvent is 1,2-dichloroethane.

7. The Method according to claim 1, wherein in step (i) X of Formula (2C) is Br and the solvent is tetrahydrofuran, X of Formula (2C) is Br and the solvent is dioxane, or X of Formula (2C) is Cl and the solvent is toluene, or X of Formula (2C) is Br and the solvent is ethyl acetate.

8. The Method according to claim 1, wherein in step (i) comprises heating (RS)-4-[5-(3,5-dichlorophenyl)-5-(trifluoromethyl)-4H-isoxazol-3-yl)]-2-methyl-benzoic acid with the compound of Formula (2A), (2B) or (2C) in the solvent to an elevated temperature.

9. The Method according to claim 1, wherein in step (ii) the separation of the precipitate from step (i) from the supernatant solution is carried out via filtration.

10. The Method according to claim 1, wherein in step (iii) the aqueous acidic solution is an aqueous solution of an inorganic acid.

11. The Method according to claim 1, wherein in step (iv) the separation of (S)-4-[5-(3,5-dichlorophenyl)-5-(trifluoromethyl)-4H-isoxazol-3-yl)]-2-methyl-benzoic acid from the acidic aqueous solution of step (iii) is carried out by an extraction with an organic solvent.

12. The Method according to claim 1, wherein (S)-4-[5-(3,5-dichlorophenyl)-5-(trifluoromethyl)-4H-isoxazol-3-yl)]-2-methyl-benzoic acid in step (iv) has an enantiomeric excess (ee) of at least 75%.

13. The Method according to claim 1, wherein the method further comprises step (v) of recrystallizing (S)-4-[5-(3,5-dichlorophenyl)-5-(trifluoromethyl)-4H-isoxazol-3-yl)]-2-methyl-benzoic acid.

14. The Method according to claim 1, comprising a further step (vi) of reacting the supernatant solution with an alkaline compound in a second organic solvent.

15. The Method according to claim 1, wherein (S)-4-[5-(3,5-dichlorophenyl)-5-(trifluoromethyl)-4H-isoxazol-3-yl)]-2-methyl-benzoic acid is further reacted with a compound according to Formula (4)

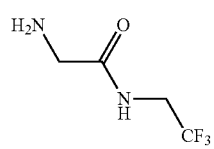

to give 4-[(5S)-5-(3,5-Dichlorphenyl)-4,5-dihydro-5-trifluormethyl-1,2-oxazol-3-yl]-N-[2-oxo-2-(2,2,2-trifluorethylamino)ethyl]-o- toluamide according to Formula (3)

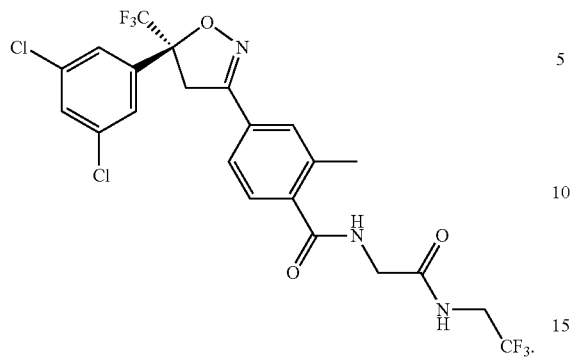
Formula (1)
16. The method of claim 14, wherein the second organic solvent is the same as the organic solvent having a polarity $E_T(30)$ between 130 and 175 kJ/mol of step (i).
* * * * *